United States Patent
Rangwalla

(10) Patent No.: US 10,302,621 B2
(45) Date of Patent: May 28, 2019

(54) METHODS FOR CHARACTERIZING BRANCHING DISTRIBUTION IN POLYMERS

(71) Applicant: ExxonMobil Chemical Patents Inc., Baytown, TX (US)

(72) Inventor: Hasnain Rangwalla, Katy, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 196 days.

(21) Appl. No.: 15/486,016

(22) Filed: Apr. 12, 2017

(65) Prior Publication Data

US 2017/0363605 A1 Dec. 21, 2017

Related U.S. Application Data

(60) Provisional application No. 62/350,223, filed on Jun. 15, 2016.

(51) Int. Cl.
| | |
|---|---|
| G01N 33/44 | (2006.01) |
| B01D 15/18 | (2006.01) |
| B01D 15/34 | (2006.01) |
| B01D 15/42 | (2006.01) |
| B01D 15/16 | (2006.01) |

(52) U.S. Cl.
CPC ......... *G01N 33/442* (2013.01); *B01D 15/161* (2013.01); *B01D 15/1878* (2013.01); *B01D 15/34* (2013.01); *B01D 15/424* (2013.01)

(58) Field of Classification Search
None
See application file for complete search history.

(56) References Cited

U.S. PATENT DOCUMENTS

| | | |
|---|---|---|
| 7,985,593 B2 | 7/2011 | Gillespie et al. |
| 9,095,792 B2 | 8/2015 | Winniford et al. |

FOREIGN PATENT DOCUMENTS

WO 2015/123164 8/2015

OTHER PUBLICATIONS

Liu et al., "Bimodal Polyethylene Products from UNIPOL Single Gas Phase Reactor Using Engineered Catalyst," 195 Macromolecular Symposia, 2003, pp. 309-316.
Xue et al., "Comparison of Chain Structures Between High-Speed Extrusion Coating Polyethylene Resins by Preparative Temperature Rising Elution Fractionation and Cross-Fractionation," Chinese Journal of Polymer Science, Zhongguo Huaxuehui, CN, 2015, vol. 33, No. 11, pp. 1586-1597.

(Continued)

*Primary Examiner* — Xiaoyun R Xu
(74) *Attorney, Agent, or Firm* — Kevin M Faulkmer

(57) ABSTRACT

New metrics are disclosed for characterizing polyethylene copolymers which can be computed from the Cross-Fractionation Chromatography data of these polymers. These metrics are able to quantify the Broad Orthogonal Composition Distribution (BOCD) character of the polymers, and they can be used to discriminate polymers with an enhanced BOCD character from polymers that have the BOCD character to a lesser extent or from polymers that have the conventional molecular weight distribution and/or branching distribution.

14 Claims, 5 Drawing Sheets

(56) References Cited

OTHER PUBLICATIONS

Wang et al., "Temperature rising Elution Fractionation and Characterization of Ethylene/Octene-1 Copolymers Synthesized with Constrained Geometry Catalyst," Macromolecular Chemistry and Physics, Wiley-VCH Verlag, Weinheim, DE, 1999, vol. 200, No. 9, pp. 2146-2151.
Xu et al., "Application of Temperature Rising Elution Fractionation in Polyolefins," European Polymer Journal, Pergamon Press Ltd., Oxford, GB, 2000, vol. 36, No. 5, pp. 867-878.
Wild et al., "Determination of Branching Distributions in Polyethylene and Ethylene Copolymers," Journal of Polymer Science Part B: Polymer Physics, John Wiley & Sons, Inc., US, 1982, vol. 20, No. 1, pp. 441-455.

METHODS FOR CHARACTERIZING BRANCHING DISTRIBUTION IN POLYMERS

PRIORITY CLAIM

This application claims priority of and the benefit of U.S. Ser. No. 62/350,223, filed Jun. 15, 2016 and is incorporated by reference in its entirety.

FIELD OF THE INVENTION

The present invention(s) relate to methods of determining the branching characteristics in polymers, and in particular to determine the comonomer composition distribution in polyolefins.

BACKGROUND

It can be desirable for polyethylene copolymers to possess a broad orthogonal composition distribution ("BOCD"), as this may enhance the stiffness, toughness, and processability (S/T/P) balance of the polyethylene and compositions that include these polymers. Given that polymers are a blend of molecules having a distribution of different chain-lengths, polymers having BOCD are branched polymers that have a preponderance, if not all, of any branching that may occur on the high molecular weight molecules of the polymer, making them less crystalline. This microstructure has a tendency to improve certain properties of products made from such BOCD-type polymers. For example, in film grades of linear low density polyethylene ("LLDPE") with the BOCD microstructure, improved processability (e.g., higher $I_{21}/I_2$) is achieved without sacrificing toughness (e.g., dart impact) and stiffness (e.g., tensile moduli) in comparison to LLDPE's that lack BOCD structure. Analogously, properties such as Slow Crack Growth Resistance are improved for pressure-pipe and blow-molding grades (esp. high density polyethylene, "HDPE") that have a bimodal molecular-weight distribution with a "reversed comonomer distribution" structure, or BOCD-type structure.

Ziegler-Natta ("ZN") produced polyethylenes tend not to have a BOCD-type structure, most of the short-chain branching being on the low molecular weight portion of the molecules thus produced. Metallocene polyethylenes, on the other hand, often do have BOCD-type structure. The value of BOCD polymers relative to conventional polymers is significant. Accordingly, any methodology enabling quantification of BOCD character in a non-trivial manner will certainly have a dramatic impact on the ability to develop new products, gain structure-property insights, and guide catalyst discovery.

A challenge in developing such methodology has been in designing appropriate characterization methods and metrics that are sensitive to the level of such microstructure attributes (i.e., "BOCD-ness" vs "ZN-ness", etc.). The Cross-Fractionation Chromatography ("CFC") technique discussed in WO 2015/123164 A1 provides a measure of the bivariate mass distribution ("BVMD") of the crystallized portion of polyethylene copolymers, and it is well-suited to elucidate the BOCD nature of such resins. Often, a visual examination of the BVMD contour plot is sufficient to confirm that the distribution is BOCD-like as opposed to the conventional ZN-type, such as is shown in FIG. 1. Such an evaluation consists of a non-quantitative method of ordering the polyethylene copolymers under consideration by increasing or decreasing BOCD-like character based on the "tilt" of the BVMD contours in the 2D plane; for example, in FIG. 1 the slope of the line in (a) is less than 0 (negative "tilt") whereas the slope of the line in (b) is greater than 0 (positive "tilt"), and this allows one to conclude that (a) has more BOCD-like character than (b).

WO 2015/123164 A1 discloses a method called "Equal-Halves Analysis" ("EHA") to obtain the weight-average temperatures ($Tw_1$ and $Tw_2$) and weight-average molecular weights ($Mw_1$ and $Mw_2$) of the polymer divided in half by mass; the differences and ratios of these metrics in conjunction with the MIR are able to differentiate resins with superior S/T/P attributes from others. However, the method has certain drawbacks, including (1) the EHA method is conceived for distributions that are separated along a temperature axis and hence these metrics are not universally applicable; and (2) the method excludes fractions below a cutoff in weight percent for which the signal-to-noise ratio is too low for Gel Permeation Chromatography ("GPC") data processing.

It would be desirable to utilize the entire BVMD with contributions from all molecular weight fractions even if their molecular-weight averages are not typically reportable using GPC alone. What is needed is an improved method of determining the BOCD attribute of polymers, especially polyethylenes.

Relevant documents also include U.S. Pat. No. 7,985,593, U.S. Pat. No. 9,095,792, and H. T. Liu et al. "Bimodal Polyethylene Products from UNIPOL™ Single Gas Phase Reactor Using Engineered Catalyst", in 195 MACROMOLECULAR SYMPOSIA 309-316 (2003).

SUMMARY

Disclosed is a method of polymer analysis comprising providing first and second chromatographic columns in series, at least one of which elutes polymer as a function of crystallizability, as represented by crystallization temperature, melting temperature, or dissolution temperature ("T"); and the other column elutes polymer as a function of its molecular weight ("M") characteristics; eluting a polymer through the first column to form elution fractions, followed by eluting the fractions through the second column; detecting the polymer fractions exiting the second column and calculating the molecular weight distributions of the polymer fractions; calculating a two dimensional distribution of the polymer molecules with a T axis and an M axis; calculating the Covariance of the eluting fractions by:

$$\text{Covariance} = \iint_{0,0}^{\infty,\infty} (T-Tw)(M-Mw)w_M(T,M)dTdM$$

wherein T is the gradient (dissolution temperature or solubility) at which the polymer fraction dissolves; $T_w$ is the weight-average dissolution temperature of the whole polymer; M is the molecular mass of a polymer fraction; $M_w$ is the weight-average molecular weight of the whole polymer; $w_M(T, M)$ is the BVMD; and wherein the Covariance can be calculated for each polymer as integrated over all the BVMD.

DETAILED DESCRIPTION

Figure 1A:
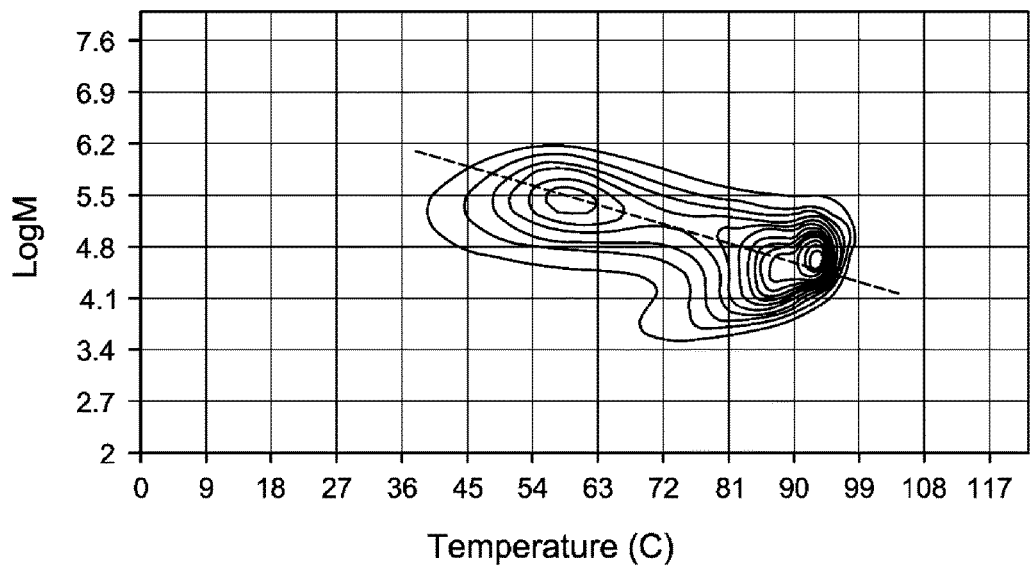
FIG. 1(a) and FIG. 1(b) exemplifies the "tilt" and "spread" in temperature elution fractionation (TREF) data of two LLDPEs: a) BOCD (metallocene produced) and b) conventional (Ziegler-Natta produced), where the dashed, guide-to-the-eye lines roughly connect the two main peaks and are qualitative indicators of the tilt of the branching distribution; the slope of the line in (a) is less than 0 (negative tilt) whereas the slope of the line in (b) is greater than 0 (positive tilt).
Figure 1B:
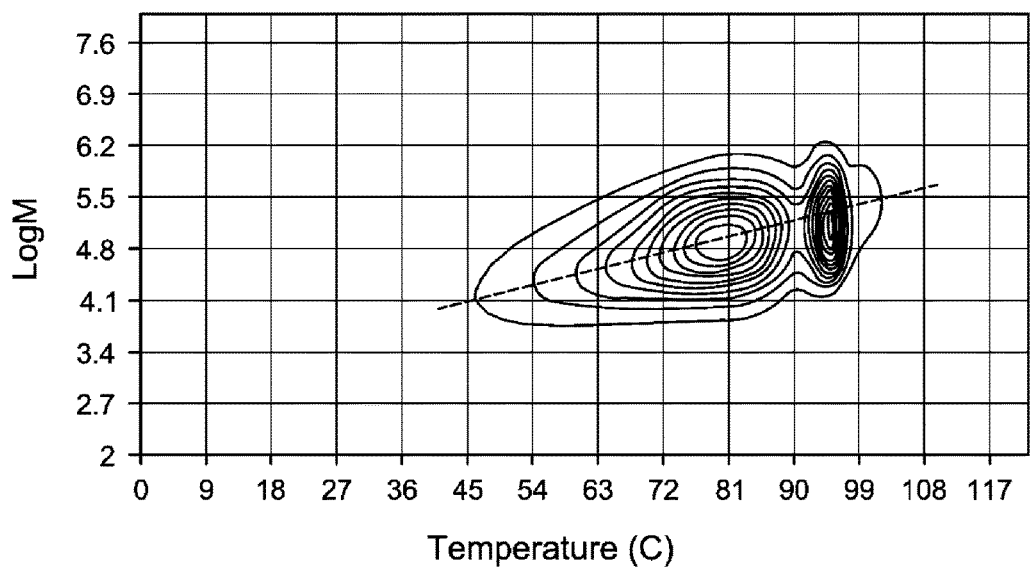
Figure 2A:
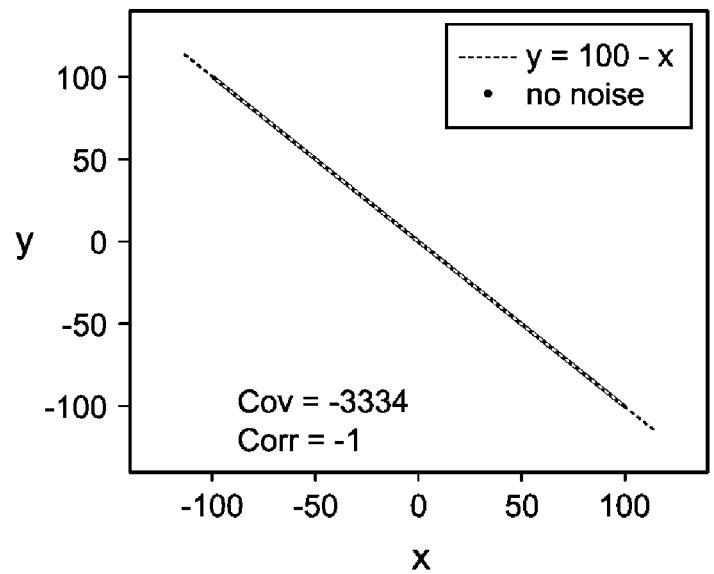
FIG. 2(a), FIG. 2(b), FIG. 2(c), and FIG. 2(d) show four sets of simulated x-y data in which the dots are generated by adding some Gaussian noise to the x and y coordinates of the points along the dashed line forming the line of negative slope.
Figure 2B:
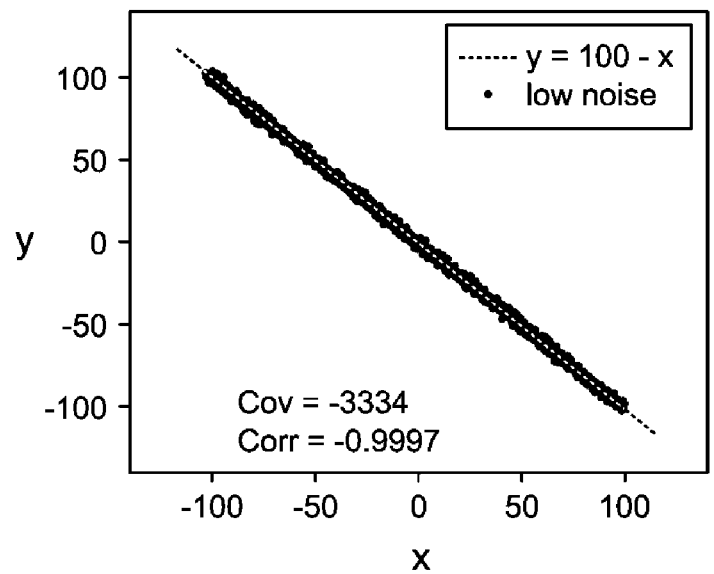
Figure 2C:
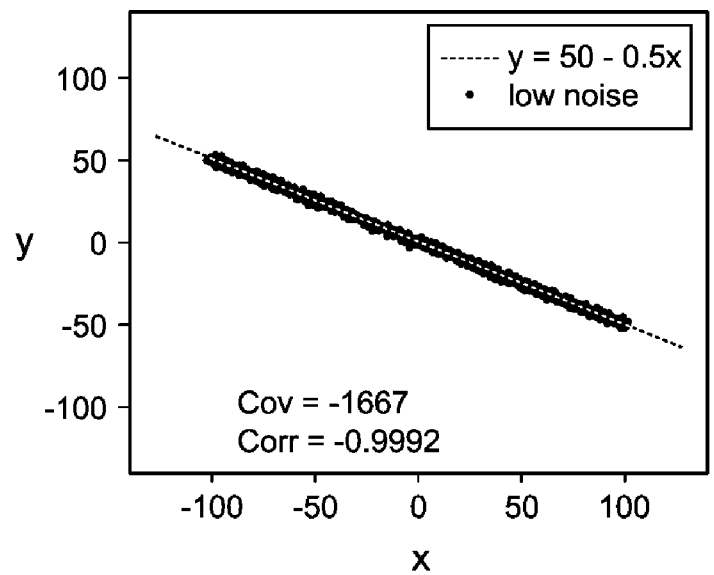
Figure 2D:
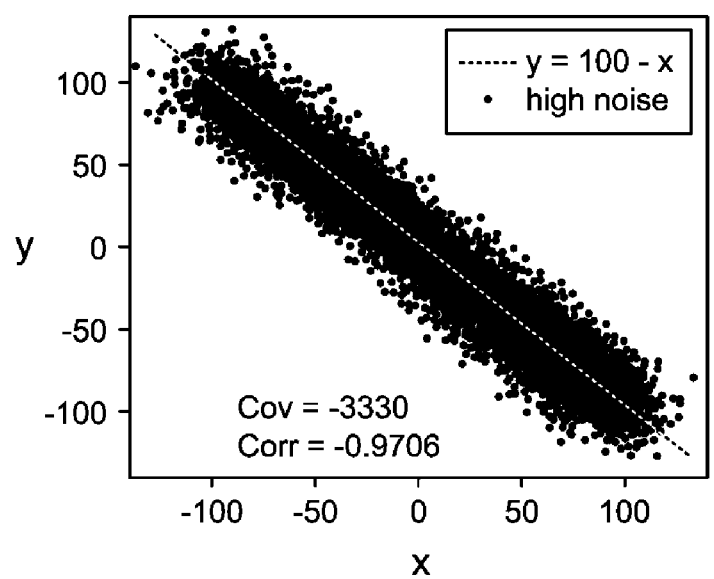

Because the BVMD obtained from CFC analysis can be converted to a joint probability density function ("PDF") for temperature T (in Kelvin) and molar mass M (kg/mole), the following mixed moments are proposed as new metrics for polymer characterization: Covariance (a central mixed moment) and the Pearson's Correlation coefficient or Pearson's "r" (denoted herein as "Correlation"), which is a normalized version of the Covariance. The Covariance ("Cov") and Correlation ("Corr") are negative for negative tilt (BOCD-type polymers) and positive for positive tilt as in FIG. 1, respectively. The magnitude and sign of the Covariance indicates level of BOCD-ness, and the magnitude of the Correlation ($\leq 1$) indicates the amount of spread in the BVMD (the magnitude increases and approaches 1 as the spread decreases). These new metrics can discriminate polymeric microstructures based on the degree of BOCD character, and in conjunction with the rheological properties, new polymers with a superior S/T/P balance can be discriminated. Moreover, these quantities are easily obtained from the BVMD of polymers, especially polyethylene copolymers by a fully automated computation and with minimal assumptions.

Thus, disclosed in any embodiment is a method of polymer analysis comprising providing first and second chromatographic columns in series, at least one of which elutes polymer as a function of dissolution temperature or solubility, or "crystallizability" ("T"), or the ability or state at which a polymer assumes a solid crystalline form, as represented by crystallization temperature (the temperature at which the polymer assumes such form), melting temperature (the temperature at which the crystalline polymer becomes non-crystalline), dissolution temperature (the temperature at which the crystal becomes non-crystalline and dissolves in a solvent), elution temperature (for temperature-gradient interactive chromatography or TGIC), solvent gradient or elution volume or elution time (for solvent-gradient interactive chromatography or SGIC), or by any other acceptable measure of crystallizability; and the other column elutes polymer as a function of its molecular weight ("M") characteristics; eluting a polymer through the first column to form elution fractions, followed by eluting each of the fractions from the first column, in any order, through the second column to obtain an independent analysis by the second column for each of the fractions from the first; detecting the polymer exiting the second column and calculating the molecular weight distributions of the polymer fractions from the first column; calculating a two dimensional distribution of the polymer molecules with a "T" axis and an "M" axis; calculating the Covariance of the eluting fractions by (1):

$$\text{Covariance} = \iint_{0,0}^{\infty,\infty} (T-T_w)(M-M_w) w_M(T,M) dT dM, \quad (1)$$

wherein "T" is the temperature at which the polymer fraction dissolves; "$T_w$" is the weight-average dissolution temperature of the crystallizing portion of the whole polymer; "M" is the molecular mass of a polymer fraction; "$M_w$" is the weight-average molecular weight of the crystallizing portion of the whole polymer; and "$w_M$ (T, M)" is the bivariate mass distribution (BVMD), which can be obtained by combining the individual chromatograms from the second column and excluding the chromatogram of the first polymer fraction which elutes at the lowest temperature and which has polymer that did not crystallize at the lowest temperature to which the polymer solution is cooled. Since M is the molecular weight of a polymer fraction exiting as a slice from the GPC (or other) column, it is understood (assumed) to be monodisperse—that is, M is the molecular weight of the slice of eluent exiting the GPC column and each slice is monodisperse. The fractions ($T_i$) of the polymer in each slice do have an $Mn(T_i)$ and an $Mw(T_i)$ since the fractions are separately analyzed by GPC, and the overall polymer has an Mn and Mw.

Desirably, the Covariance is calculated for each polymer as integrated over all the BVMD for the crystallizing portion of the whole polymer. Of course, it is known that there is a "purge" or non-crystallizing portion of the polymer, such as described by Nakano and Goto in "Development of Automatic Cross Fractionation: Combination of Crystallizability Fractionation and Molecular Weight Fractionation" in 26 J. APPL. POLY. SCI. 4217-4131 (1981).

Note that in any embodiment the "dissolution temperature" could also be called crystallization temperature or a quantity that is indicative of the crystallization temperature as is known in the art, or the run length of segments in polymer molecules that can be incorporated in crystals.

In any embodiment, the first column either utilizes a temperature control device or is operated using multiple solvents (i.e., "interactive chromatography") with or without the device for controlling temperature; and wherein the second column is a GPC column. In another embodiment, the order can be reversed and the first column is a GPC column, the second being a column that separates by crystallizability, such as a TREF column.

In any embodiment, the detecting step further includes obtaining the molecular weight characteristics at each elution volume slice by GPC using any suitable detectors (e.g., Differential Refractive Index (DRI), Light Scattering (LS) and/or Infrared (IR) detector, or any combination thereof, with or without a viscometer).

In any embodiment, a Correlation can be calculated, wherein the Correlation is the Covariance/$\sigma_T \cdot \sigma_M$, where (4):

$$\sigma_T^2 = \iint_{0,0}^{\infty,\infty} (T-T_w)^2 w_M(T,M) dT dM,$$

$$\sigma_M^2 = \iint_{0,0}^{\infty,\infty} (M-M_w)^2 w_M(T,M) dT dM. \quad (4)$$

In any embodiment, the first chromatographic column elutes polymer as a function of dissolution temperature by varying the temperature of the column, and the second chromatographic column elutes as a function of MW.

In a particular embodiment the BVMD may be obtained in the form $w_z$ (T', z), where T' is the temperature in Celcius and $z=\log_{10}$ (M') and M' is the molecular weight in gm/mole. The BVMD $w_M$ (T, M) with T in Kelvin and M in kg/mole can then be obtained by a simple change of variables as shown in (5).

$$w_M(T, M) = \frac{w_z(T - 273.15, \log M + \log 1000)}{\ln 10 \times M}. \quad (5)$$

In any embodiment, the first chromatographic column elutes polymer as a function of solvent composition and/or having an interactive stationary phase such as in high performance liquid chromatography (HPLC), and the second chromatographic column elutes as a function of MW. In any embodiment, the bivariate mass distribution (BVMD), $w_M$, for each elution fraction is a function of solvent composition and molecular weight (T, M).

In any embodiment, the polymer is a polyethylene. Desirably, the polyethylene has a density of 0.93, or 0.925, or 0.92 g/cm$^3$ or less, or within a range from 0.93, or 0.925, or 0.92 g/cm$^3$ to 0.88, or 0.87 g/cm$^3$. The polyethylene can be made by any polymerization method known such as a slurry, solution, high pressure, or gas phase process, or any combination thereof. The polyethylene can also be made using any catalyst, for example, a single-site catalyst known such as a metallocene, a salen compound, a pyridyldiamide compound, or other single-site organo-metallic compound, or so-called ZN-type catalysts, or any combination of two or more catalysts, for example, two or more metallocene catalysts can be used together or in series. In any embodiment, the polyethylene is produced using a Ziegler-Natta catalyst or a single-site catalyst.

In any embodiment the Covariance is a negative value, indicating a polyethylene having broad orthogonal distribution. In any embodiment, such polyethylene is produced by a single-site catalyst.

Also disclosed in any embodiment is a chromatographic system comprising (i) at least a TREF column and/or an HPLC column, and (ii) a GPC column, and having detectors such that the output is captured by a computing system comprising code to convert the output into the Covariance and/or Correlation by the methods described herein. As used herein, a "computer" or "computing system" is a general purpose device or collection of devices ("system") that can be coded or programmed to carry out a set of arithmetic or logical operations automatically, and is capable of either manual data input or automatic acceptance of data from a source or output such as a chromatographic detector.

The BVMD is of the form $w_z$(T',z); T' is temperature in ° C.; $z=\log_{10}$ M' and M' is the molecular weight in gm/mole such as in FIG. 1. The form of this distribution can be converted to the above-mentioned joint PDF by a change of variables such as T'→T and z→M where T is the temperature in Kelvin (K) units (T'=T−273.15) and M is the molecular weight in kg/mole $z=\log_{10}$(M×1000) (because here the base "b" in the expression $\log_b \alpha$ will always be 10, the base can be dropped, and z=log M+log1000). The $w_z$ value is often provided by the instrumentation used. Any units can be chosen, but here units are chosen for mathematical convenience. The variable transformations are set forth here (6):

$$dT = dT' \quad (6)$$

$$dz = \frac{dM}{\ln 10 \times M}$$

$$\therefore w_M(T, M) dT dM = \frac{w_z(T - 273.15, \log M + \log 1000)}{\ln 10 \times M} dT dM$$

$$\therefore w_M(T, M) = \frac{w_z(T - 273.15, \log M + \log 1000)}{\ln 10 \times M}.$$

To facilitate the computation of the inventive metrics, a two-dimensional raw-moment function of integer variables i and j is defined as follows (7):

$$\mu_{i,j} \equiv \mu(i,j) = \iint_{0,0}^{\infty,\infty} T^i M^j w_M(T,M) dT dM. \quad (7)$$

Because $w_M$(T,M) is a PDF, $\mu_{0,0}=1$, note that (8):

$T_w$(weight-average elution temperature)$=\mu_{1,0}$, and $M_w$(weight-average molecular weight)$=\mu_{0,1}$, (8)

from the definition of $\mu_{i,j}$ and the definitions of the following four quantities (9):

$$\text{Covariance} = \iint_{0,0}^{\infty,\infty} (T - T_w)(M - M_w) w_M(T, M) dT dM,$$

$$\text{Correlation} = \frac{\text{Covariance}}{\sigma_T, \sigma_M},$$

$$\sigma_T^2 = \iint_{0,0}^{\infty,\infty} (T - T_w)^2 w_M(T, M) dT dM, \text{ and}$$

$$\sigma_M^2 = \iint_{0,0}^{\infty,\infty} (M - M_w)^2 w_M(T, M) dT dM,$$

the following can be obtained:

$$\text{Covariance} = \mu_{1,1} - T_w M_w, \text{ and} \quad (9)$$

$$\text{Correlation} = \frac{\text{Covariance}}{\sqrt{\mu_{2,0} - (T_w)^2} \sqrt{\mu_{0,2} - (M_w)^2}}.$$

Also, the various moments can be computed by using $w_z$ (T', z) directly (without conversion), as here (10):

$$\mu_{i,j} = \iint_{-\infty,-273.15}^{\infty,\infty} (T'+273.15)^i (10^z)^j w_z(T',z) dT' dz. \quad (10)$$

Specifically, the $\mu_{i,j}$'s can be computed by a simple trapezoidal integration of the digitized BVMD, as provided for example by the chromatography instrument software. A table of $\mu_{i,j}$'s can be generated (spanning a range of i and j) for only the crystalline portion of the BVMD; the soluble fraction ("SF") is ignored because the temperature of the SF does not have a clear physical meaning. This means that for the range of the definite integrals that are outside the range of temperature and molecular weight indicated by the crystalline portion of the BVMD, the PDF is taken to have a value of 0. Typically, in the CFC analysis of PE copolymers under cryogenic conditions (crystallizing down to 0° C. or below) the SF has a negligible mass fraction, so this truncation of the BVMD is justified for such CFC analyses. Because the SF is ignored and also due to numerical round off, $\mu_{0,0}$ is usually $\neq 1$; therefore, each $\mu_{i,j}$ is normalized (divided by $\mu_{0,0}$) before using it in the calculation of any of the derived quantities. For example (11), $$T_w = \frac{\mu_{1,0}}{\mu_{0,0}}. \qquad (11)$$

To illustrate the effectiveness of the inventive metrics, consider the simulated data shown in FIG. 2(a), FIG. 2(b), FIG. 2(c), and FIG. 2(d). The Covariance term is calculated as $(x-\langle x \rangle)(y-\langle y \rangle)$ for each (x, y) data point simulated, and by definition (12):

$$\text{Cov} = \frac{1}{N}\sum_{i=0}^{N} (\text{Covariance term})_i = \frac{1}{N}\sum_{i=0}^{N} (x-\langle x \rangle)(y-\langle y \rangle),$$

where N=number of points simulated, and:

$$\text{Corr} = \text{Cov} \bigg/ \left(\left(\frac{1}{N}\sum_{i=0}^{N}(x-\langle x \rangle)^2\right)\left(\frac{1}{N}\sum_{i=0}^{N}(y-\langle y \rangle)^2\right)\right). \qquad (12)$$

In each plot in FIG. 2(a), FIG. 2(b), FIG. 2(c), and FIG. 2(d), the level of noise (standard deviation of the Gaussian noise) and the slope of the dashed line are varied; also, the Covariance ("Cov"), the Correlation (Corr), and the averages $\langle x \rangle$ and $\langle y \rangle$ of the simulated data are reported. In FIG. 2, note that the Covariance terms are negative for a distribution that has a negative "tilt" because when $x<\langle x \rangle$, $y>\langle y \rangle$, and vice versa; accordingly, for a positive "tilt" these terms will be positive; and for horizontal and vertical distributions these terms will be negligible in magnitude. Also note that the Correlation ("Corr") is sensitive to the noise and is lower for more noisy data. Although not shown in this figure, the Covariance is 0 for a slope of 0, decreases monotonically to a minimum of −3334 as slope decreases to −1, then increases monotonically back to 0 as slope decreases to −∞ (vertical line); starting from a slope of 0, the Covariance increases monotonically to 3334 as slope increases to 1, then decreases monotonically back to 0 as slope increases to ∞ (vertical line). This simplified example demonstrates that the "tilt" and "spread" of a BVMD can be quantified by using the magnitude and sign of these new metrics; in particular, a BOCD-like BVMD should have a negative Covariance, a Ziegler-Natta-like BVMD should have a positive Covariance, and a BCD-like or a BMD-like BVMD should have a small (near-zero) Covariance.

The various descriptive elements and numerical ranges disclosed herein for the inventive methods can be combined with other descriptive elements and numerical ranges to describe the invention(s); further, for a given element, any upper numerical limit can be combined with any lower numerical limit described herein, including the examples. The features of the inventions are demonstrated in the following non-limiting examples.

EXAMPLES

Cross-fractionation chromatography ("CFC"), which combines TREF and traditional GPC ("TREF/GPC") as disclosed in WO 2015/123164 A1,was performed on a CFC-2 instrument from Polymer Char, Valencia, Spain. The instrument was operated and subsequent data processing, for example, smoothing parameters, setting baselines, and defining integration limits, was performed according to the manner described in the CFC User Manual provided with the instrument or in a manner commonly used in the art. The instrument was equipped with a TREF column (stainless steel; o.d., 3/8"; length, 15 cm; packing, non-porous stainless steel micro-balls) in the first dimension and a GPC column set (3×PLgel 10 μm Mixed B column from Polymer Labs, UK) in the second dimension. Downstream from the GPC column was an infrared detector (IR4 from Polymer Char) capable of generating an absorbance signal that is proportional to the concentration of polymer in solution.

The sample to be analyzed was dissolved in ortho-dichlorobenzene, at a concentration of about 5 mg/ml, by stirring at 150° C. for 75 min Then a 0.5 ml volume of the solution containing 2.5 mg of polymer was loaded in the center of the TREF column and the column temperature was reduced and stabilized at about 120° C. for 30 min. The column was then cooled slowly (0.2° C./min) to 30° C. (for ambient runs) or −15° C. (for cryogenic runs) to crystallize the polymer on the inert support. The low temperature was held for 10 min before injecting the soluble fraction into the GPC column. All GPC analyses were done using solvent ortho-dichlorobenzene at 1 ml/min, a column temperature of 140° C., and in the "Overlap GPC Injections" mode. Then the subsequent higher-temperature fractions were analyzed by increasing the TREF column temperature to the fraction set-points in a stepwise manner, letting the polymer dissolve for 16 min ("Analysis Time"), and injecting the dissolved polymer into the GPC column for 3 min ("Elution Time"). The soluble portion or "purge" of the polymers was not analyzed, only the "insoluble" portion of the polymer samples were analyzed, that is, insoluble at −15° C. or lower.

The universal calibration method was used for determining the molecular mass of eluting polymers. Thirteen narrow molecular-weight distribution polystyrene standards (obtained from Polymer Labs, UK) within the range of 1.5 to 8,200 Kg/mol were used to generate a universal calibration curve. Mark-Houwink parameters were obtained from Appendix I of *Size Exclusion Chromatography* by S. Mori and H. G. Barth (Springer, 1999). For polystyrene K=1.38× $10^{-4}$ dl/g and α=0.7; and for polyethylene K=5.05×$10^{-4}$ dl/g and α=0.693 were used. Fractions having a weight % recovery (as reported by the instrument software) of less than 0.5% were not processed for calculations of molecular-weight averages (Mn, Mw, etc.) of the individual fractions or of aggregates of fractions.

Figure 3:
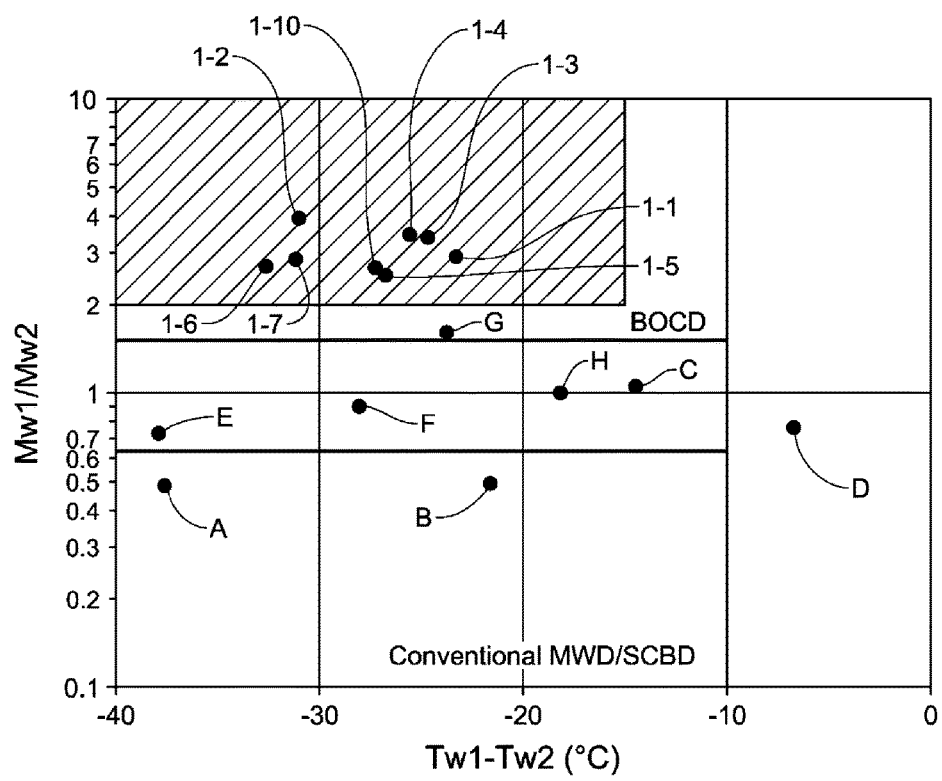
FIG. 3 is a graph of the Equal Halves Analysis of CFC data as provided in Table 9 of WO 2015/123164 A1, where the polymers A to G are for various control polymers that either don't have the BOCD character or have it to a lesser extent; the shaded box shows a portion of the region in which the polymers with BOCD character must lie; and the polymers 2-1 to 7-10 are for polymers having BOCD character, whereas the 1-1 and 1-10 do not.
Figure 4A:
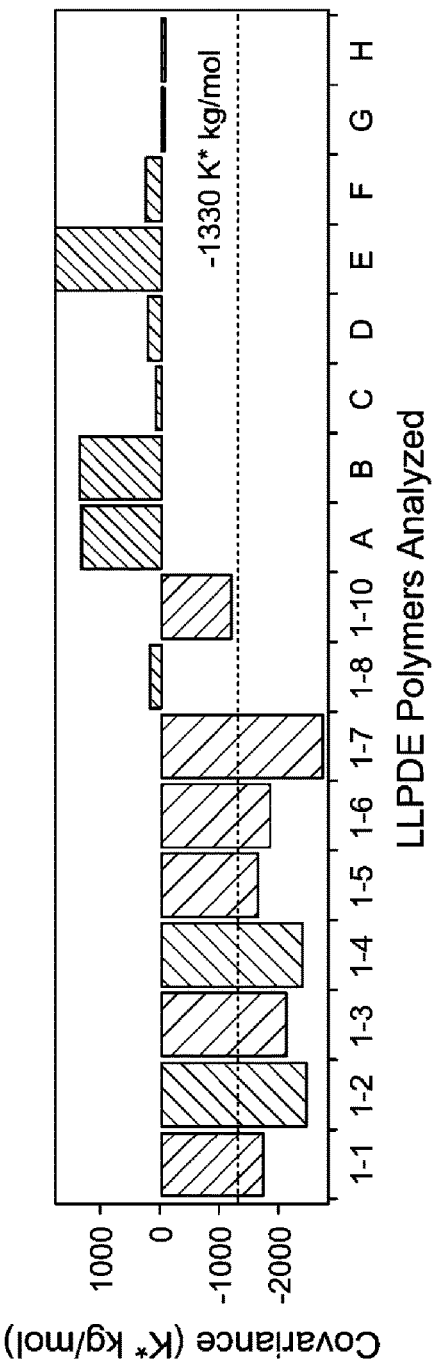
FIG. 4(a) and FIG. 4(b) is a graph of the inventive Covariance and Correlation metrics computed for the polymers shown in FIG. 3; the polymer 1-8 does not appear in FIG. 3 because it was not included in the source of the data for that figure; where the solid bars are for negative values (more BOCD character) and patterned bars are for positive values (more conventional character); the dotted lines in (a) and (b) show cutoff values discussed in the text.
Figure 4B:
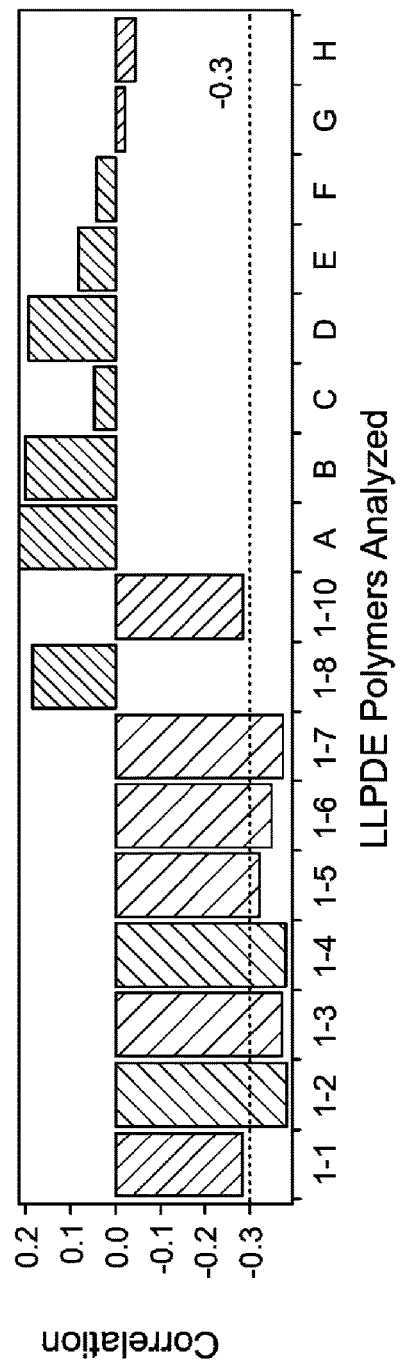

The fractionation data in WO 2015/123164 A1, especially as described in paragraphs [0141] to [0158], summarized in Table 9, and graphically represented in FIG. 6A, FIG. 6B, and FIG. 7 were used in the inventive examples described here. As an application to real data, polyethylenes were plotted as in FIG. 3 for which the Equal-Halves Analysis was performed as described in WO 2015/123164 A1. In this analysis, the weight-average temperatures and molecular weights of two halves of the BVMD of a polymer are determined, and a point obtained from these values, for the polymer, is plotted in a 2-D graph as shown in FIG. 3. The graph area is divided into sub-areas that indicate whether the polymer has the BOCD character or if it has the conventional molecular weight and chain-branching distribution character. Several polyethylenes with BOCD character were found to be within a sub-area of the BOCD region. FIG. 4 shows the inventive Covariance and Correlation computed for all of the polymers in FIG. 3. Clearly, the dotted line in FIG. 4 shows a cutoff value that can be chosen to establish the necessary condition for a polymer to have the desired amount of BOCD character: the Covariance must be less than or equal to the cutoff for the polymer to be considered as having a BOCD; alternatively, the dotted line in (b) can also be chosen for increased specificity (only the BOCD polymers are below the line).

The inventive Covariance and Correlation could also similarly apply to a GPC/TREF system, as well as an HPLC/GPC system.

Where the doctrine of "incorporation by reference" applies, all of the test methods, patent publications, patents and reference articles are hereby incorporated by reference either in their entirety or for the relevant portion for which they are referenced.

The invention claimed is:

1. A method of polymer analysis comprising:
   a) providing first and second chromatographic columns in series, at least one of which elutes polymer as a function of crystallizability, as represented by crystallization temperature, melting temperature, or dissolution temperature (T); and the other column elutes polymer as a function of its molecular weight (M) characteristics;
   b) eluting a polymer through the first column to form elution fractions, followed by eluting each of the fractions from the first column, in any order, through the second column to obtain an independent analysis by the second column for each of the fractions from the first;
   c) detecting the polymer exiting the second column and calculating the molecular weight distributions of the polymer fractions from the first column;
   d) calculating a two dimensional mass distribution of the polymer molecules with an axis for the crystallizability (T) and an M axis;
   e) calculating the Covariance of the eluting fractions by:

$$\text{Covariance} = \iint_{0,0}^{\infty,\infty}(T-Tw)(M-Mw)w_M(T,M)dTdM$$

wherein:
   T is the gradient (dissolution temperature or solubility) at which the polymer fraction dissolves;
   $T_w$ is the weight-average dissolution temperature of the whole polymer;
   M is the molecular weight of a polymer fraction;
   $M_w$ is the weight-average molecular weight of the whole polymer;
   $w_M$ (T, M) is the bivariate mass distribution (BVMD) of the crystalline portion of the polymer; and
   f) wherein the Covariance is calculated for each polymer as integrated over all the BVMD.

2. The method of claim 1, wherein the first column either is temperature controlled and/or is operated using multiple solvents; and wherein the second column is a GPC column.

3. The method of claim 1, wherein the detecting step further includes obtaining the M characteristics at each elution volume slice by GPC using any suitable detectors.

4. The method of claim 1, calculating the Correlation, wherein the Correlation is the Covariance/$\sigma_T \cdot \sigma_M$, where:

$$\sigma_T^2 = \iint_{0,0}^{\infty,\infty}(T-Tw)^2 w_M(T,M)dTdM,$$

$$\sigma_M^2 = \iint_{0,0}^{\infty,\infty}(M-Mw)^2 w_M(T,M)dTdM.$$

5. The method of claim 1, wherein the first chromatographic column elutes polymer as a function of dissolution temperature by varying the temperature of the column, and the second chromatographic column elutes as a function of M.

6. The method of claim 1, wherein the bivariate mass distribution (BVMD), $w_M$, for each elution fraction is a function of temperature gradient and the logarithm to the base 10 of molecular weight (z) (T, z) and the Covariance is described by:

$$\text{Covariance} = \iint_{-\infty,0}^{\infty,\infty}(T-Tw)(z-z_w)w_z(T,z)dTdz$$

wherein:
T is the gradient (dissolution temperature or solubility) at which the polymer fraction dissolves;
$T_w$ is the weight-average dissolution temperature of the whole polymer;
z is the logarithm to the base 10 of molecular weight of a polymer fraction;
$z_w$ is the weight-average molecular weight of the whole polymer;
$w_z$ (T, z) is the bivariate mass distribution (BVMD) of the crystalline portion of the polymer; and
wherein the Covariance is calculated for each polymer as integrated over all the BVMD.

7. The method of claim 1, wherein the first chromatographic column elutes polymer as a function of solvent composition and/or having an interactive stationary phase, and the second chromatographic column elutes as a function of M.

8. The method of claim 7, wherein the bivariate mass distribution (BVMD), $w_M$, for each elution fraction is a function of solvent composition and molecular weight.

9. The method of claim 1, wherein the polymer is a polyethylene.

10. The method of claim 9, wherein the polyethylene has a density of 0.93 g/cm³ or less.

11. The method of claim 9, wherein the polyethylene is produced using a Ziegler-Natta catalyst or a single-site catalyst.

12. The method of claim 9, wherein the Covariance is a negative value, indicating a polyethylene having BOCD.

13. The method of claim 1, wherein the polymer comprises less than 10 wt % soluble fraction.

14. A chromatographic system comprising (i) at least a TREF column and/or an HPLC column, and (ii) a GPC column, and having detectors such that the output is captured by a computing system comprising code to convert the output into the Covariance and/or Correlation by the method of claim 1.

* * * * *